United States Patent [19]

Arnaudet et al.

[11] Patent Number: 4,642,337
[45] Date of Patent: Feb. 10, 1987

[54] NOVEL URANIUM COMPOUNDS, THEIR PREPARATION PROCESS AND THEIR USE AS CATALYSTS FOR THE HYDROGENATION OF UNSATURATED ORGANIC COMPOUNDS

[75] Inventors: Lucile Arnaudet, Paris; Gérard Folcher, Orsay, both of France

[73] Assignee: Commissariat a l'Energie Atomique, Paris, France

[21] Appl. No.: 715,176

[22] Filed: Mar. 22, 1985

[30] Foreign Application Priority Data

Mar. 29, 1984 [FR] France ................. 84 04928

[51] Int. Cl.$^4$ ..................... C07F 5/00; B01J 31/00
[52] U.S. Cl. ..................... 534/11; 502/152; 534/10
[58] Field of Search ............ 534/10, 11; 556/53, 556/143, 43, 47, 60; 585/275; 502/152

[56] References Cited

U.S. PATENT DOCUMENTS 3,920,745 11/1975 Floriani et al. ............... 585/275

OTHER PUBLICATIONS

P. J. Fagan et al., "Synthesis and Properties of Bis(pentamethylcyclopentadienyl) Actinide Hydrocarbyls and Hydrides, A New Class of Highly Reactive f-Element Organometallic Compounds", JACS, 1981, 103, pp. 6650–6667.
Journal of the American Chemical Society, vol. 95, No. 1, 10 janvier 1973, pp. 91–93; A. E. Gebala et al; "Alpha-Bonded Organometallic Compounds of Uranium (IV)", *p. 91, abstract; p. 93, alinea 3*.

Primary Examiner—John F. Terapane
Assistant Examiner—Virginia Caress

[57] ABSTRACT

Novel uranium compounds, their preparation process and their use as catalysts for the hydrogenation of unsaturated organic compounds.

The uranium compounds are in accordance with formula:

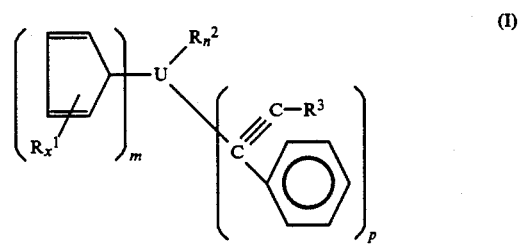

in which $R^1$ represents an alkyl group, $R^2$ an alkyl group, $R^3$ an alkyl or aryl group, x is equal to 0 or is an integer between 1 and 5, m is equal to 1, 2 or 3, n is equal to 0, 1 or 2, p is equal to 1 or 2, provided m+n is equal to 3.

They can be used as catalysts for the hydrogenation of organic compounds, such as olefins, preferably dissolved in an organic solvent, such as tetrahydrofuran.

12 Claims, No Drawings

NOVEL URANIUM COMPOUNDS, THEIR PREPARATION PROCESS AND THEIR USE AS CATALYSTS FOR THE HYDROGENATION OF UNSATURATED ORGANIC COMPOUNDS

BACKGROUND OF THE INVENTION

The present invention relates to novel uranium compounds, a process for the preparation thereof and their use as catalysts for the hydrogenation of unsaturated organic compounds, particularly olefins.

Olefin hydrogenation processes usually use heterogeneous catalysis and hydrogenation catalysts based on precious metals on inert supports.

Although these heterogeneous catalysis processes are widely used industrially and give good results, there is now a significant interest in homogeneous catalysis methods using soluble complexes for finding solutions to hydrogenation problems necessitating a certain selectivity.

Thus, the mechanisms occurring in homogeneous catalysis involves interactions between the olefin and a metal within a dissolved complex, and the nature of the metal as the structure of the complex are determinative elements for the development of the reaction. Generally, the metals used in these complexes are series d transmission metals, particularly metals of the platinum and palladium series. However, the use of such metals is disadvantageous due to their very high price and their scarceness.

Consideration has also been given to the use of other metals and for some years now there has been considerable interest in uranium compounds with a low degree of oxidation, because it has been found that, although the properties of uranium are far removed from those of precious metals, certain uranium III compounds have an affinity for olefins, as is described in the article in J. CHEMICAL, Soc., Chem. Commun, 1982, pp. 323/4.

Moreover, uranium is very easy to work up, is very inexpensive in the depleted state and is available in a very pure form, because the nuclear industry requires a high degree of purity.

However, this affinity is not observed for all uranium III compounds, e.g. in the case of compound $(C_5H_5)_3U$.

In the same way, the standard uranium compounds such as $(C_5H_5)_3UCH_3$, $(C_5H_5)_3UCl$ and $(C_8H_8)_2U$ do not interact with the molecules to be activated, because they are either too stable, or are coordination number saturated. Other uranium compounds have also been investigated which are more difficult to prepare as a result of their instability, particularly trivalent uranium derivatives, which are soluble in organic solvents, which is not the case with uranium derivatives of type $(C_5H_5)_3U$.

SUMMARY OF THE INVENTION

The present invention relates to novel uranium III compounds having the aforementioned characteristics.

The uranium III compounds according to the invention comply with the formula:

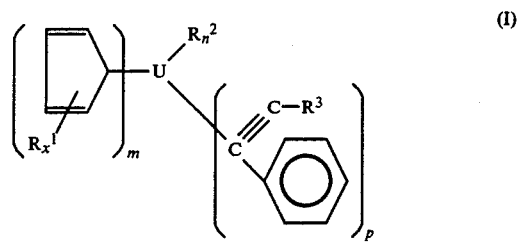

in which $R^1$ represents an alkyl group, $R^2$ an alkyl group, $R^3$ an alkyl or aryl group, x is equal to 0 or is an integer between 1 and 5, m is equal to 1, 2 or 3, n is equal to 0, 1 or 2, p is equal to 1 or 2, provided that m+n is equal to 3.

In the case of the compounds according to the invention, there is an interaction between the uranium atom and the acetylene derivative of formula $C_6H_5—C≡C—R^3$, which is completely unexpected, because no other uranium derivative, or element of group f has the capacity to fix an acetylene compound by a $\pi$ bond.

As a result of this interaction, it is possible to produce in solution a type which is catalytically active for the hydrogenation of olefins. This property has already been studied in the case of titanium, as is illustrated by U.S. Pat. No. 3,920,745. However, it was highly unlikely that the uranium can be activated in this way, because it is not supposed to react with acetylene derivatives.

Examples of uranium compounds which comply with formula (I), reference is made to compounds in accordance with the following formulas:

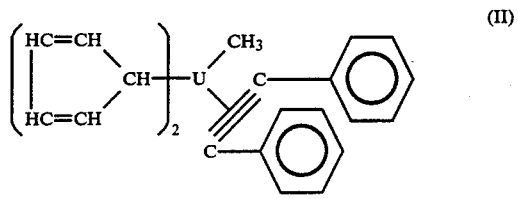

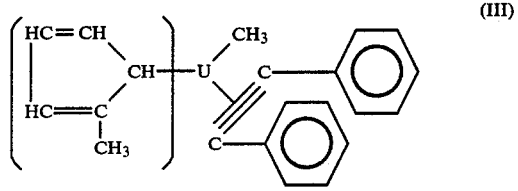

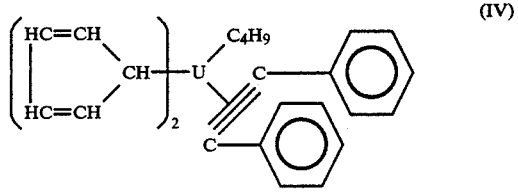

The invention also relates to a process for the preparation of uranium compounds in accordance with formula (I).

This process consists of reacting a uranium compound of formula: $(C_5H_{5-x}R_x^1)_3UCl$ in which $R^1$ represents an alkyl group and x is equal to 0 or is an integer between 1 and 5, with a lithium compound of formula LiR², in which R² represents an alkyl group, and an acetylene derivative of formula C₆H₅—C≡C—R³, in which R³ represents an alkyl or aryl group.

During this reaction, firstly an alkyl group R² is fixed to the uranium IV compound, followed by a reduction of the uranium and a uranium III derivative of formula $(C_5H_{5-x}R^1_x)_2UR^2$ is obtained. Following this reaction, the uranium III compound is able to fix one or two molecules of the acetylene derivative and in this way the uranium compound of formula (I) is obtained.

This reaction is generally performed in a solvent constituted by an organic compound having at least one ether-oxide function, e.g. in tetrahydrofuran or ethyl ether. This leads to the compound according to the invention dissolved in said solvent, but it can be separated by conventional methods, e.g. by evaporating the solvent.

In the invention, the alkyl radicals R¹, R² and R³ are generally straight or branched alkyl radicals with 1 to 5 carbon atoms, e.g. methyl, butyl, propyl, i-propyl radicals. The aryl radicals which can be used are phenyl, naphthyl, tolyl, xylyl and similar radicals. Moreover, it is possible to use in the present invention, compounds in which the two cyclopentadienyl groups fixed to the uranium atom are different, one of the two groups having for example a hydrogen atom substituted by an alkyl group. Thus, the uranium can be made chiral and an optical selectivity can be obtained on the molecules to be hydrogenated.

The compounds according to the invention dissolved in a solvent constituted by an organic compounds having at least one ether-oxide function, such as tetrahydrofuran or ethyl ether, can be used as catalysts for the hydrogenation of unsaturated organic compounds, e.g. olefins.

In this case, it is assumed that the first stage is a hydrogenation of the acetylene derivative fixed to the uranium atom and said derivative gives way in the uranium coordination shell to the olefin, which is in turn activated and then hydrogenated. Thus, in these catalysts, the uranium coordination shell is already occupied by several ligands: cyclopentadienyl, alkyl, whereof it is possible to vary the structure so as to determine the geometry of the coordination number site and in this way obtain a high specificity.

The invention also relates to a process for the hydrogenation of unsaturated organic compounds, which consists of reacting at least one olefin with hydrogen in the presence of a catalyst containing the compound of formula (I). Advantageously, the catalyst is constituted by a solution of said compound in a solvent formed by an organic compound having at least one ether-oxide function, such as tetrahydrofuran or ethyl ether.

The compound used as the solvent can be inert with respect to the products present for the reaction. The hydrogenation reaction can be carried out at ambient temperature and at atmospheric pressure.

The unsaturated organic compounds which can be hydrogenated by the process according to the invention are ethylene or acetylene unsaturation compounds, which do not react with the catalyst, e.g. olefins, such as ethylene, propylene, etc and diolefins such as butadiene, isoprene, phenyl butadiene, etc.

Other features and advantages of the invention can be gathered from the study of the following examples, which are obviously given in an illustrative and non-limitative manner.

EXAMPLE 1

(a) Preparation of a catalyst based on (C₅H₅)₂UCH₃(C₆H₅—C≡C—C₆H₅)

1 g of

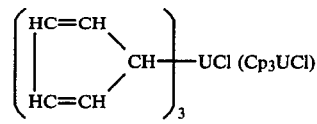

is dissolved in 10 ml of tetrahydrofuran (THF). This is followed by the addition of 130 mg of LiCH₃ and the reaction medium is stirred. After stirring for 1 hour, 0.34 g of diphenyl acetylene is added to the reaction medium, which gives a catalyst containing the uranium compound:

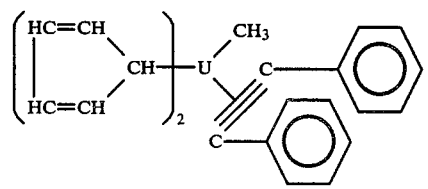

The structure of this compound was checked by NMR.

(b) Hydrogenation of the ethylene

Ethylene is introduced into 200 cc of the solution obtained in stage (a) under a partial pressure of 13.5 kPa. This is followed by liquid nitrogen trapping to retain the ethylene in the solution. Hydrogen is then introduced under a partial pressure of 13.5 kPa and the temperature is allowed to return to ambient temperature.

The gas given off is chromatographically analysed and at the end of 2 hours, half the ethylene has been converted into ethane. At the end of the operation, it is checked that the catalyst has remained intact by nuclear magnetic resonance.

EXAMPLE 2

The same catalyst as in example 1 is used and the ethylene is introduced under a partial pressure of 1.3 kPa into a volume of 250 cc of the catalyst solution, the liquid nitrogen is trapped and then hydrogen is introduced under a partial pressure of 54 kPa. The temperature is allowed to return to ambient temperature and by chromatographic analysis it is established that all the ethylene has been converted into ethane after 2 hours.

EXAMPLE 3

Here again, use is made of the same catalyst as in example 1 and the propylene is hydrogenated under the same conditions using a propylene pressure of 13.5 kPa and a hydrogen pressure of 13.5 kPa. After 2 hours, half the propylene has been converted into propane.

EXAMPLE 4

(a) Preparation of a catalyst based on (C₅H₅)₂UC₄H₉(C₆H₅—C≡C—C₆H₅)

1 g of Cp₃UCl is dissolved in 10 ml of THF, followed by the addition to the solution of 384 mg of LiC₄H₉ and the mixture is then stirred. After stirring for 1 hour, 0.34 g of diphenyl acetylene is added and this leads to a solution containing:

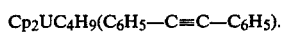

Cp$_2$UC$_4$H$_9$(C$_6$H$_5$—C≡C—C$_6$H$_5$).

(b) Hydrogenation of the ethylene

The ethylene is hydrogenated using the catalyst under the same conditions as in example 1. After 2 hours, half the ethylene has been hydrogenated to ethylene.

EXAMPLE 5

(a) Preparation of a catalyst based on (C$_5$H$_4$CH$_3$)$_2$UCH$_3$(C$_6$H$_5$—C≡C—C$_6$H$_5$)

Firstly, (C$_5$H$_4$CH$_3$)$_3$UCl is prepared by reacting (C$_5$H$_4$CH$_3$)Na on uranium tetrachloride in tetrahydrofuran. 1 g of (C$_5$H$_4$CH$_3$)$_3$UCl is then dissolved in 10 ml of THF and 130 mg of LiCH$_3$ are added. Stirring takes place and after stirring for 1 hour, 0.34 g of diphenylene acetylene is added. This gives a solution of:

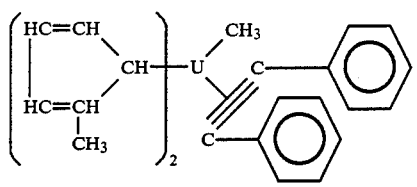

in tetrahydrofuran.

(b) Hydrogenation of the ethylene

The catalyst is used under the same conditions as in example 1 for carrying out the hydrogenation of the ethylene and after 2 hours, half the ethylene has been converted into ethane.

What is claimed is:

1. A uranium compound in accordance with formula:

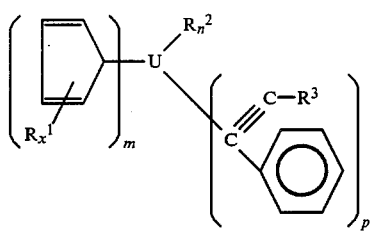

(I)

in which R$^1$ represents a straight or branched alkyl group having 1 to 5 carbon atoms, R$^2$ is a straight or branched alkyl group having 1 to 5 carbon atoms, R$^3$ is a straight or branched alkyl group having 1 to 5 carbon atoms or a phenyl, naphthyl, tolyl or xylyl radical, x is equal to 0 or is an integer between 1 and 5, m is equal to 1, 2 or 3, n is equal to 0, 1 or 2, p is equal to 1 or 2, provided that m+n is equal to 3.

2. A compound according to claim 1 in accordance with formula:

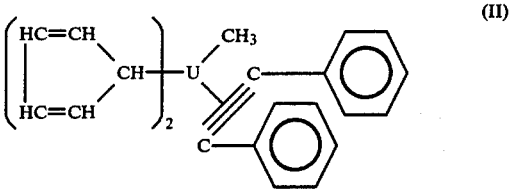

(II)

3. A compound according to claim 1 in accordance with formula:

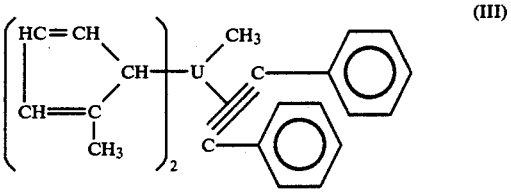

(III)

4. A compound according to claim 1 in accordance with formula:

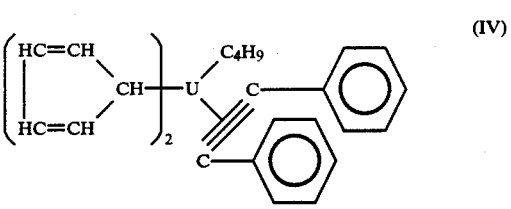

(IV)

5. A process for the preparation of a uranium compound according to any one of the claims 1, 2, 3, or 4, wherein a uranium compound of formula:

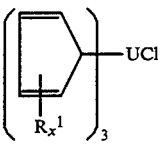

in which R$^1$ represents a straight or branched alkyl group having 1 to 5 carbon atoms and x is equal to 0 or is an integer between 1 and 5 is reacted with a lithium compound of formula LiR$^2$, in which R$^2$ represents a straight or branched alkyl group having 1 to 5 carbon atoms, and an acetylene derivative of formula C$_6$H$_5$≡C—R$^3$ in which R$^3$ represent a straight or branched alkyl group having 1 to 5 carbon atoms or a phenyl, naphthyl, tolyl or xylyl radical.

6. A process according to claim 5, wherein the reaction is carried out in a solvent constituted by an organic compound containing at least one ether-oxide function.

7. A process according to claim 6, wherein the solvent is tetrahydrofuran or ethyl ether.

8. A catalyst for the hydrogenation of unsaturated organic compounds, wherein it is constituted by the product of the reaction of a compound of formula:

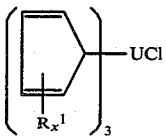

with $LiR^2$ and $C_6H_5C{\equiv}CR^3$, in which $R^1$ and $R^2$ represent a straight or branched alkyl group having 1 to 5 carbon atoms, $R^3$ represents a straight or branched alkyl group having 1 to 5 carbon atoms or a phenyl, naphthyl, tolyl or xylyl radical and x is equal to 0 or is an integer between 1 and 5, in a solvent constituted by an organic compound having at least one ether-oxide function.

9. A catalyst according to claim 8, wherein x is equal to 0, $R^2$ represents $CH_3$ and $R^3$ represents $C_6H_5$.

10. A catalyst according to claim 8, wherein x is equal to 0, $R^2$ represents $C_4H_9$ and $R^3$ represents $C_6H_5$.

11. A catalyst according to claim 8, wherein x is equal to 1, $R^1$ and $R^2$ represent $CH_3$ and $R^3$ represents $C_6H_5$.

12. A catalyst according to claim 8, wherein the solvent is tetrahydrofuran.

* * * * *